United States Patent
Miura

(10) Patent No.: US 8,776,578 B2
(45) Date of Patent: Jul. 15, 2014

(54) GAS SENSOR

(75) Inventor: Tadamasa Miura, Nagaokakyo (JP)

(73) Assignee: Murata Manufacturing Co., Ltd., Nagaokakyo-Shi, Kyoto-fu (JP)

( * ) Notice: Subject to any disclaimer, the term of this patent is extended or adjusted under 35 U.S.C. 154(b) by 591 days.

(21) Appl. No.: 13/090,871

(22) Filed: Apr. 20, 2011

(65) Prior Publication Data

US 2011/0209527 A1    Sep. 1, 2011

Related U.S. Application Data

(63) Continuation of application No. PCT/JP2009/070230, filed on Dec. 2, 2009.

(30) Foreign Application Priority Data

Dec. 2, 2008   (JP) ................. 2008-307797

(51) Int. Cl.
G01N 25/00    (2006.01)

(52) U.S. Cl.
USPC ....... 73/25.05; 73/25.01; 73/31.05; 73/31.06; 338/22 R; 338/23; 338/22 SD

(58) Field of Classification Search
USPC ................. 73/25.01, 25.05, 31.06
See application file for complete search history.

(56) References Cited

U.S. PATENT DOCUMENTS

| | | | |
|---|---|---|---|
| 4,030,340 A * | 6/1977 | Chang | 73/31.01 |
| 4,134,818 A * | 1/1979 | Pebler et al. | 204/406 |
| 7,548,149 B2 | 6/2009 | Miura et al. | |
| 2001/0000298 A1 * | 4/2001 | Wienand et al. | 338/25 |
| 2003/0056570 A1 * | 3/2003 | Shin et al. | 73/25.05 |
| 2007/0212263 A1 | 9/2007 | Shin et al. | |
| 2007/0227575 A1 * | 10/2007 | Kato et al. | 136/224 |
| 2008/0048821 A1 | 2/2008 | Miura et al. | |
| 2009/0167482 A1 | 7/2009 | Miura et al. | |
| 2011/0259083 A1 * | 10/2011 | Lee et al. | 73/31.05 |
| 2013/0255358 A1 * | 10/2013 | LEE et al. | 73/31.06 |

FOREIGN PATENT DOCUMENTS

| | | | | |
|---|---|---|---|---|
| JP | 61-083948 A | | 4/1986 | |
| JP | 62235555 A | | 10/1987 | |
| JP | 63173943 A | * | 7/1988 | G01N 27/12 |
| JP | 06-260302 A | | 9/1994 | |
| JP | 2003083058 A | | 3/2003 | |
| JP | 2005098846 A | | 4/2005 | |
| JP | 2005300522 A | | 10/2005 | |
| JP | 2012058067 A | * | 3/2012 | |
| WO | WO-2006085507 A1 | | 8/2006 | |

OTHER PUBLICATIONS

English Translation of JP 2005—098846.*

* cited by examiner

*Primary Examiner* — Hezron E Williams
*Assistant Examiner* — Alexander Mercado
(74) *Attorney, Agent, or Firm* — Dickstein Shapiro LLP

(57) ABSTRACT

A gas sensor having high detection sensitivity and a low output signal noise includes a laminate of thermistor ceramic, a catalytic electrode, an internal electrode, and external electrodes. When coming into contact with a detection target gas, the catalytic electrode generates heat, and the resistance of a thermistor layer of a sensing portion is decreased. Since the heat generated by the catalytic electrode is directly transferred to the thermistor layer without passing through an insulating layer or the like, high detection sensitivity is obtained. In addition, the structure can be formed in which heat of the sensing portion is insulated by a hollow portion and heat diffusion is prevented, so that the heat capacity of the sensing portion is further decreased.

18 Claims, 3 Drawing Sheets

FIG. 1 – Prior Art
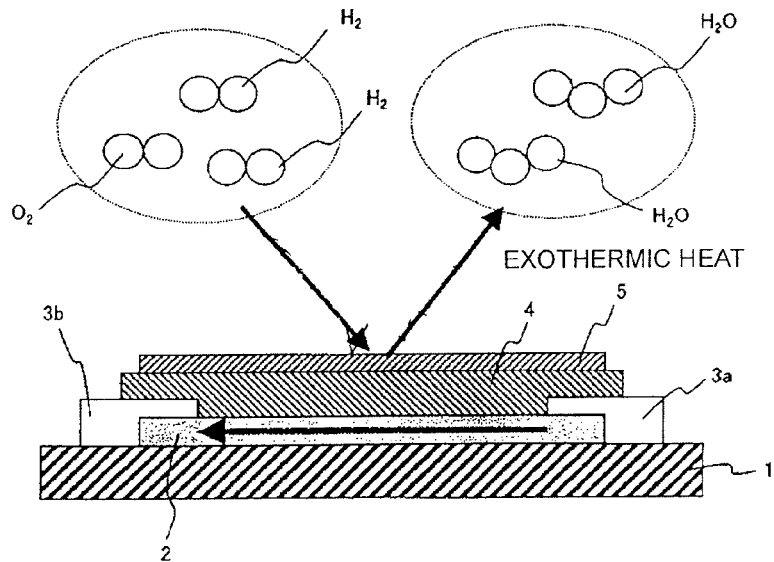
FIG. 2
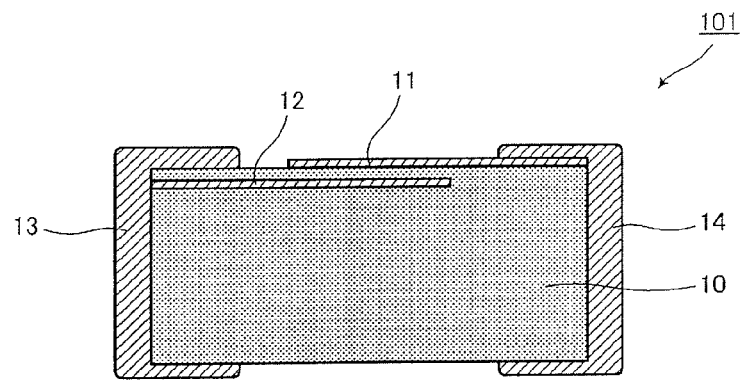
FIG. 3
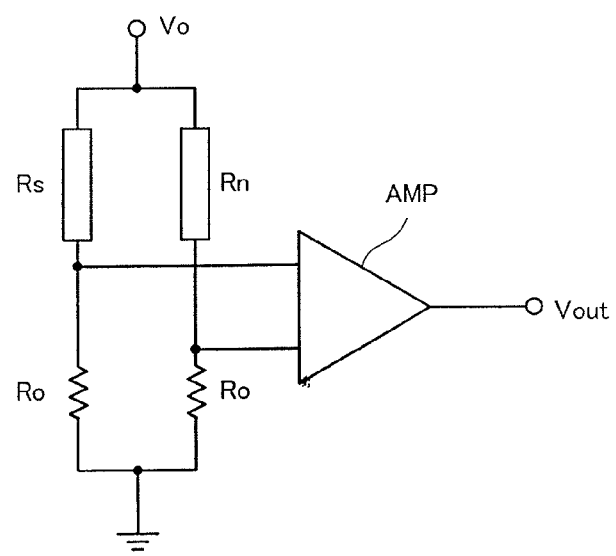

GAS SENSOR

This is a continuation of application Ser. No. PCT/JP2009/070230, filed Dec. 2, 2009, the entire content of which are hereby incorporated herein by reference.

TECHNICAL FIELD

The present invention relates to a gas sensor which detects a flammable gas such as a hydrogen gas, and more particularly relates to a gas sensor which detects a detection target gas by converting exothermic heat or endothermic heat generated by a catalyst into the change in resistance of a thermistor.

BACKGROUND ART

There are various gases whose detection is desired. Examples include exhaust gases emitted from automobiles, the emission amount of which is regulated, toxic gases discharged from home hot-water heaters under abnormal conditions, and gases used for fuel cells which have been developed in order to overcome recent environmental problems.

For example, there may be mentioned $CO_2$, $NO_x$, and $SO_x$ in the exhaust gases emitted from automobiles, CO as a toxic gas discharged from home hot-water heaters, and $H_2$ as a gas discharged from fuel cells. In particular, since gas leakage of CO, $H_2$, and the like may cause serious accidents, a gas sensor which can accurately and rapidly detect a detection target gas has been increasingly demanded as time progressed.

For example, since $H_2$ has a low explosion limit of 4%, a hydrogen gas sensor for fuel cells is required to rapidly detect a small amount of gas. Being used under severe conditions, this type of sensor is also required to have excellent environmental resistance. Furthermore, in order to promote wide spread of fuel cells, inexpensive sensors have also been desired.

Several gas sensors using exothermic heat or endothermic heat generated by a catalytic reaction of a noble metal, such as Pt or Pd, have been proposed. In particular, a gas sensor which detects a detection target gas by converting the heat of an exothermic or an endothermic reaction performed in a catalytic layer into a temperature-dependent resistance value of a thermistor has been disclosed in Patent Document 1.

With reference to FIG. 1, the operation of the gas sensor disclosed in Patent Document 1 will be described.

As shown in FIG. 1, the gas sensor of Patent Document 1 includes on a substrate 1 used as a support member, a thermistor layer 2, electrodes 3a and 3b connected to two ends thereof so as to flow current in the thermistor layer 2 in parallel with a film surface thereof, an insulating layer 4 formed on the thermistor layer 2 and the electrodes 3a and 3b to prevent a short circuit between the electrodes 3a and 3b, and a catalytic layer 5 formed on the insulating layer 4.

The electrodes 3a and 3b are connected to the two ends of the thermistor layer 2 with a predetermined gap therebetween so as to have flow current in the thermistor layer 2 in parallel with the film surface thereof. As a material for the electrodes 3a and 3b, for example, there may be mentioned a metal material, such as aluminum or platinum, which is used for common electrodes.

The insulating layer 4 is a layer which prevents short circuit between the electrodes 3a and 3b, and for example, an insulating resin or ceramic may be used.

The catalytic layer 5 is formed of a material which causes an exothermic or an endothermic reaction upon interaction with a detection target gas, and for example, an oxidation catalytic material which catalyzes oxidation of a detection target gas or a hydrogen storing alloy may be used.

Patent Document 1: Japanese Unexamined Patent Application Publication No. 2005-98846

PROBLEMS TO BE SOLVED BY THE INVENTION

In Patent Document 1, the structure includes the thermistor layer 2, the insulating layer 4, and the catalytic layer 5 provided in this order from a bottom side, and the catalytic layer 5 and the thermistor layer 2 are electrically insulated from each other. The reason for this is that since the catalytic layer 5 is a noble metal layer, an electrical signal cannot be extracted (the electrical resistance of the catalytic layer becomes dominant) if the insulating layer is not provided.

In this case, the insulating layer 4 disturbs heat conduction, and there has been a problem in that high detection sensitivity is not easily obtained.

In addition, the thermistor layer 2 is a thin film formed on the substrate 1, and the electrical resistance is to be detected in a plane direction of the thin film in the structure disclosed in Patent Document 1. Since the thermistor layer 2 is a thin film, the cross-sectional area thereof is small, and the resistance thereof is high. Hence, the output signal noise is disadvantageously increased.

Furthermore, since a thermal separation between the thermistor layer 2 and the substrate 1 is difficult to achieve, according to the structure disclosed in Patent Document 1, heat applied to the thermistor layer 2 is transferred to the substrate 1 by heat conduction. As a result, there has been a problem in that high detection sensitivity is not easily obtained.

Hence, an object of the present invention is to provide a gas sensor having high detection sensitivity and a low output signal noise.

MEANS FOR SOLVING THE PROBLEMS

In order to achieve the above object, a gas sensor of the present invention has the following structure. The gas sensor comprises a laminate which includes a plurality of electrodes and a plurality of thermistor layers, at least one of the plurality of electrodes is a catalytic electrode which is disposed at a surface of the laminate and catalyzes an exothermic or an endothermic reaction when coming into contact with a detection target gas, and at least one of the plurality of electrodes is an internal electrode which is disposed so that at least one of the plurality of thermistor layers is between the internal electrode and the catalytic electrode.

By the structure described above, no insulating layer is provided between the catalytic electrode and the thermistor layer, and the exothermic heat or endothermic heat generated by the catalytic electrode is directly transferred to the thermistor layer by heat conduction, so that high detection sensitivity can be obtained.

In addition, the resistance is appropriately low since the electrical resistance of the thermistor layer in a layer direction (thickness direction) is to be detected. Hence, output signal noise can be decreased.

A hollow portion is can further be formed inside than the internal electrode of the laminate. By this structure, thermal separation can be achieved between a sensing portion formed of the catalytic electrode and the thermistor layer in which the temperature is changed by the exothermic or endothermic heat generated by the catalytic electrode and a portion of the laminate located further inside than the sensing portion. Hence, the heat capacity of this sensing portion can be significantly decreased, and heat applied to the thermistor layer of the sensing portion is not transferred to the inside of the laminate by heat conduction. As a result, a high response can be obtained.

At least two of the plurality of electrodes can be temperature compensating internal electrodes which are disposed so that at least one of the plurality of thermistor layers is not thermally coupled with the catalytic electrode. By using such internal electrodes, temperature compensation can be performed, and stable sensitivity properties can be obtained over a wide temperature range. Furthermore, since a temperature compensating element is not additionally required, the sensor is not required to be increased in size.

A region in the laminate which is opposite to a region in which the catalytic electrode is formed with respect to one of the internal electrodes located furthest apart from the catalytic electrode may be formed of an insulating material. By this structure, the contribution of the change in resistance in a sensing region can be increased, and detection sensitivity is improved.

An external electrode may include a material which forms no ohmic contact with the thermistor layer. By this structure, the change in resistance in the thermistor layer between internal electrodes becomes dominant, the contribution of the change in resistance in a sensing region can be increased, and hence detection sensitivity is improved.

Between the catalytic electrode and the surface thermistor layer of the laminate, an ohmic electrode which forms an ohmic contact with the surface thermistor layer of the laminate may be formed. By this structure, a thermistor material which forms no direct ohmic contact with a catalytic electrode, such as a common positive temperature coefficient thermistor material, may even be used.

ADVANTAGES

According to the present invention, a gas sensor having high detection sensitivity and a low output signal noise can be formed.

BRIEF DESCRIPTION OF DRAWINGS

FIG. 1 is a view showing the structure of the gas sensor disclosed in Patent Document 1.

FIG. 2 is a cross-sectional view of a gas sensor 101 according to a first embodiment.

FIG. 3 is one example of a gas detection circuit using the gas sensor 101 according to the first embodiment.

FIRST EMBODIMENT

Figure 4:
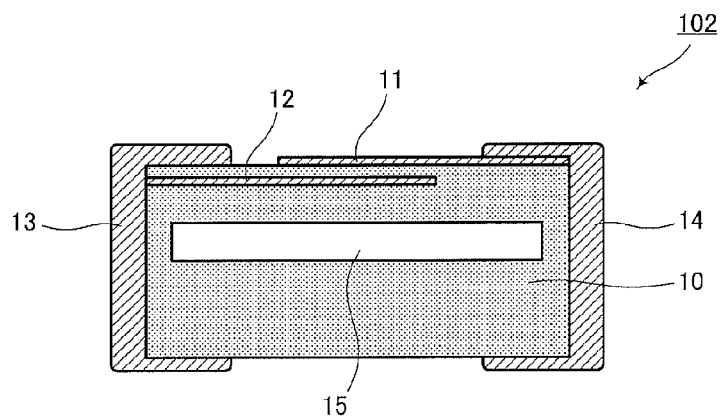
FIG. 4 is a cross-sectional view of a gas sensor 102 according to a second embodiment.

FIG. 2 is a cross-sectional view of a gas sensor 101 according to a first embodiment. The gas sensor 101 includes a laminate 10 of negative temperature coefficient (NTC) thermistor ceramics, a catalytic electrode 11, an internal electrode 12, and external electrodes 13 and 14.

In the laminate 10, a surface layer portion extending from the internal electrode 12 to an exposed portion of the catalytic electrode 11 is a sensing portion. When the catalytic electrode 11 comes into contact with a detection target gas, exothermic heat or endothermic heat is generated by a catalytic reaction. Hence, the temperature of a thermistor layer immediately under the catalytic electrode 11 is increased or decreased, and the resistance of the thermistor layer is decreased or increased.

The catalytic electrode 11 is electrically connected to the external electrode 14, and the internal electrode 12 is electrically connected to the external electrode 13. Hence, the resistance of the thermistor layer located between the catalytic electrode 11 and the internal electrode 12 is detected using the external electrodes 13 and 14. The NTC thermistor ceramic can be a sintered compact of at least two transition metal element oxides formed, for example, from Mn, Ni, Co, Fe, Cu, Al, Ti, and Zn.

The catalytic electrode 11 is formed from a material which causes an exothermic or an endothermic reaction by interaction with a detection target gas. For example, an oxidation catalytic material which catalyzes oxidation of a detection target gas may be used. By using the catalytic materials mentioned above, the gas to be detected may be appropriately selected, and vice versa. In particular, when the detection target gas is a hydrogen gas, Pt or Pd is preferably used, for example, in view of reactivity with a hydrogen gas.

The internal electrode 12 is formed from Ag, Pd, or an alloy thereof which forms an ohmic contact with an NTC thermistor ceramic. That is, since the catalytic electrode 11 forms an ohmic contact with an NTC thermistor ceramic, the catalytic electrode 11 and the internal electrode 12 may be formed from the same electrode material.

An overlapping area and distance between the catalytic electrode 11 and the internal electrode 12 are determined in consideration of the rate of change in resistance of an NTC thermistor ceramic so that the resistance between the catalytic electrode 11 and the internal electrode 12 has a desired value.

Although the catalytic electrode 11 may be formed by sputtering after sintering of the ceramic, a printing method, such as screen printing, is preferably performed before sintering of the ceramic in view of process simplification and the like. Naturally, in order to improve the catalytic efficiency, the catalytic electrode 11 may be formed of a porous material. For example, a porous electrode may be formed by addition of a binder component to a screen printing paste, or other methods may also be used. In addition, a paste for catalytic electrodes may contain as an auxiliary material a metal oxide component contained in the ceramic in order to ensure the adhesion to the ceramic.

In the gas sensor 101 having the above structure, a case in which the catalytic electrode 11 contains Pd as a primary component and where a hydrogen gas is detected will be described.

When a hydrogen gas is present in a detection target gas, the temperature of the catalytic electrode 11 is increased by a catalytic action performed on the hydrogen gas by the Pd contained in the catalytic electrode to cause an exothermic reaction. The heat of this catalytic electrode 11 increases the temperature of the thermistor layer provided between the catalytic electrode 11 and the internal electrode 12. When the change in resistance is caused by this increase in temperature is measured through the external electrodes 13 and 14, the presence of a hydrogen gas can be detected, or the concentration thereof can be quantitatively measured.

Next, an example of a particular method for manufacturing the gas sensor 101 will be sequentially described.

(a) As a ceramic raw material, a predetermined amount of $Mn_3O_4$, NiO, $Co_3O_4$, CuO, $Fe_2O_3$, $TiO_2$, $Al_2O_3$, or the like is measured and is then charged into a ball mill containing pulverization media formed, for example, of zirconia. After sufficient wet pulverization is performed, calcination is performed at a predetermined temperature, so that a ceramic powder is formed.

(b) After an organic binder is added to the ceramic powder, a wet mixing treatment is performed to form a slurry, and ceramic green sheets are then formed by a doctor blade method or the like.

(c) By using an internal-electrode paste containing Ag—Pd as a primary component, an internal electrode pattern is formed on one ceramic green sheet by screen printing. In addition, by using a Pd-electrode paste, screen printing is performed on one ceramic green sheet by a method similar to that performed for the internal electrode, so that a catalytic electrode pattern is formed.

(d) After the ceramic green sheet on which the internal electrode pattern is screen-printed is placed on the ceramic green sheet on which the catalytic electrode pattern is screen-printed, a predetermined number of ceramic green sheets on which the internal electrode pattern and the catalytic electrode pattern are not formed are laminated on the ceramic green sheet on which the internal electrode pattern is screen-printed, and are then pressure bonded so that a laminated substrate before sintering is formed.

Between the ceramic green sheet on which the internal electrode pattern is printed and the ceramic green sheet on which the catalytic electrode pattern is printed, a ceramic green sheet on which the internal electrode pattern and the catalytic electrode pattern are not printed may be provided.

(e) After the above steps (b) to (d) forming a laminated substrate which is a collective substrate formed of a plurality of laminates are performed, the laminated substrate before sintering is cut into the individual laminates 10 before sintering, and a debinder treatment is then performed on each laminate 10 received in a zirconia-made container. Subsequently, a firing treatment is performed at a predetermined temperature (for example, at 1,000° C. to 1,300° C.), so that the laminate 10 of NTC thermistor ceramics provided with the internal electrode 12 and the catalytic electrode 11 is formed.

(f) After an external-electrode paste containing Ag or the like is applied to two end portions of each laminate 10, firing is performed to form the external electrodes 13 and 14. As a result, the gas sensor 101 is manufactured by the above steps.

The external electrodes 13 and 14 preferably have good adhesion and may be formed by a thin film-forming method, such as a sputtering method or a vacuum deposition method.

In this embodiment, although an oxide, such as $Mn_3O_4$, is used as the ceramic raw material, for example, a carbonate or a hydroxide of Mn may also be used.

According to the first embodiment, the following advantages can be obtained. Since the catalytic electrode 11 functions as a catalyst and an electrode extracting an electrical signal, compared to the structure shown in FIG. 1 in which the resistance of a thin film thermistor layer is detected in a plane direction thereof, no insulating layer is required, and hence the structure can be significantly simplified. In addition, defects, such as an insulation defect of an insulating layer, never occur, and hence the reliability is improved.

Since the insulating layer is not required, thermal coupling between the thermistor layer and the catalytic electrode can be improved.

In the structure in which the resistance of a thin film thermistor layer is detected in a plane direction thereof, for example, a surface electrode is formed to have a comb teeth shape, and the resistance is adjusted by changing the number of teeth and the gap therebetween. Hence, the design range is limited, and the degree of freedom of selecting materials (in particular, the rate of change in resistance of a thermistor) is limited. On the other hand, the resistance can be adjusted by the distance (the thickness of the thermistor layer) between the catalytic electrode 11 and the internal electrode 12 and the overlapping area therebetween according to the first embodiment. Hence, the design range of resistance is significantly increased, and the degree of freedom of selecting materials is increased. In addition, since the resistance is relatively decreased, the output signal noise can be decreased.

FIG. 3 shows an example of a gas detection circuit using the above gas sensor 101. In FIG. 3, resistance Rs indicates the resistance of the thermistor of the sensing portion, and resistance Rn indicates the resistance of a temperature compensating thermistor. A resistance bridge circuit is formed by the resistances Rs and Rn and resistances Ro and Ro. An amplifying circuit AMP performs differential amplification of an output voltage of the resistance bridge circuit.

By the gas detection circuit shown in FIG. 3, the output voltage $V_{out}$ of the amplifying circuit AMP indicates a value corresponding to the resistance Rs of the thermistor. Hence, the output voltage $V_{out}$ can be used as a gas detection signal.

As described above, a detection target gas can be detected by measuring the change in resistance by an increase in temperature through the catalytic electrode 11, the internal electrode 12, and the external electrodes 13 and 14.

Although the example is described in which an NTC thermistor ceramic is used, the present invention may also be applied to the case in which a PTC thermistor ceramic is used.

SECOND EMBODIMENT

FIG. 4 is a cross-sectional view of a gas sensor 102 according to a second embodiment. The gas sensor 102 includes a laminate 10 of NTC thermistor ceramic, a catalytic electrode 11, an internal electrode 12, external electrodes 13 and 14, and a hollow portion 15. The structure other than the hollow portion 15 is similar to that of the first embodiment shown in FIG. 2.

The hollow portion 15 thermally separates the sensing portion, which includes a surface layer portion of the laminate 10 and in which the catalytic electrode and the internal electrode are located, from the other region of an element main body. This hollow portion 15 is formed in such a way that some of thermistor layers forming the laminate 10 are processed to have an opening portion and are then laminated to each other.

When the catalytic electrode 11 comes into contact with a detection target gas and generates heat thereby, the heat is also transferred to thermistor layers located opposite to the catalytic electrode with respect to the internal electrode 12; however, since the hollow portion 15 is provided in a region located further apart from the catalytic electrode, heat conduction is blocked at this place, and hence the heat is prevented from spreading over the entire laminate 10. In other words, the heat capacity of the sensing portion is small. As a result, the rate of increase in temperature of the sensing portion by a catalytic reaction of a detection target gas is increased, and a high response can be obtained.

A method for manufacturing the gas sensor 102 is substantially the same as the process shown in the first embodiment. However, a predetermined number of ceramic green sheets on which the electrode patterns are not printed are processed to form the hollow portion 15.

In order to form ceramic green sheets forming the hollow portion, holes forming the hollow portion can be provided in the ceramic green sheets, for example, by a laser or a punching process, and the holes thus formed can be filled, for example, with an organic material, such as a binder, or a carbon paste. By the steps described above, the ceramic green sheets each having a hollow pattern are formed.

In addition, a predetermined number of layers are used as the ceramic green sheets each having a hollow pattern from the ceramic green sheets on which the internal electrode patterns and the catalytic electrode patterns are not printed.

Subsequently, the ceramic green sheets are laminated in the order as shown in the step (d) of the first embodiment and are then pressure bonded to each other, so that a laminated substrate before sintering is formed.

Then, the laminated substrate thus obtained is cut into individual laminates before sintering to have predetermined dimensions, and a debinder treatment is performed on each laminate received in a zirconia-made container. Subsequently, a firing treatment is performed at a predetermined temperature (for example, at 1,000° C. to 1,300° C.). By this debinder treatment and the firing treatment, the organic material, such as a binder or the carbon paste is removed, and the portion formed by this removal functions as the hollow portion 15.

As described above, the laminate 10 including the catalytic electrode 11, the internal electrode 12, and the hollow portion 15 is formed.

Although the example is described in which an NTC thermistor ceramic is used, the present invention may also be applied to the case in which a PTC thermistor ceramic is used.

THIRD EMBODIMENT

Figure 5:
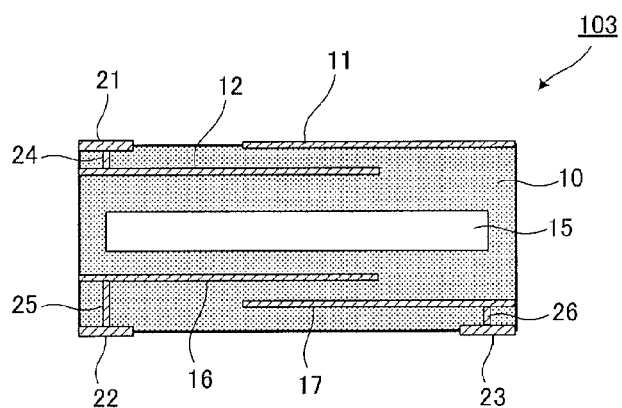
FIG. 5 is a cross-sectional view of a gas sensor 103 according to a third embodiment.

FIG. 5 is a cross-sectional view of a gas sensor 103 according to a third embodiment. The gas sensor 103 includes a laminate 10 of NTC thermistor ceramics, a catalytic electrode 11, an internal electrode 12, a surface electrode 21, a via electrode 24, temperature compensating internal electrodes 16 and 17, rear electrodes 22 and 23, via electrodes 25 and 26, and a hollow portion 15.

The surface electrode 21 is electrically connected to the internal electrode 12 through the via electrode 24. In addition, the rear electrodes 22 and 23 are electrically connected to the temperature compensating internal electrodes 16 and 17 through the via electrodes 25 and 26, respectively.

When coming into contact with a detection target gas, the catalytic electrode 11 generates heat, and the resistance between the catalytic electrode 11 and the internal electrode 12 is decreased. The catalytic electrode 11 and the surface electrode 21 are electrically connected to an external circuit by wire bonding or the like.

The facing area and distance between the temperature compensating internal electrodes 16 and 17 are the same as a facing area and distance between the catalytic electrode 11 and the internal electrode 12, respectively. Since the hollow portion 15 is provided between the pair of the catalytic electrode 11 and the internal electrode 12 and the pair of the temperature compensating internal electrodes 16 and 17, even if the catalytic electrode 11 comes into contact with a detection target gas and the temperature is increased thereby, the hollow portion insulates the heat. Hence, an ambient temperature is usual around the temperature compensating internal electrodes 16 and 17 and the vicinities thereof.

When the gas sensor 103 is mounted on a mounting portion, the rear electrodes 22 and 23 are electrically connected thereto.

When the resistance of the thermistor layer between the catalytic electrode 11 and the internal electrode 12 is regarded as the resistance Rs shown in FIG. 3, and the resistance of the thermistor layer between the temperature compensating internal electrodes 16 and 17 is regarded as the resistance Rn shown in FIG. 3, the relationship of the output voltage $V_{out}$ to the concentration of a detection target gas can be maintained constant substantially without being influenced by the change in ambient temperature.

In addition, since an additional temperature compensating element is not required, and the temperature compensating internal electrodes are integrated, the number of mounting elements is reduced. Hence, as a result, reduction in the mounting area and a reduction in temperature deviation caused by the distance between a sensing element and a temperature compensation element can be realized, and the reliability and accuracy of the sensor can be improved.

FOURTH EMBODIMENT

Figure 6:
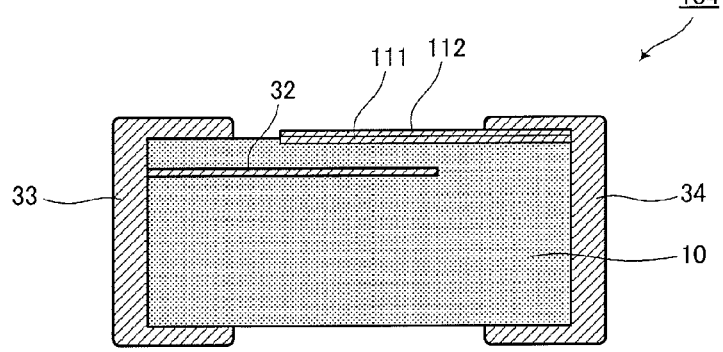
FIG. 6 is a cross-sectional view of a gas sensor 104 according to a fourth embodiment.

FIG. 6 is a cross-sectional view of a gas sensor 104 according to a fourth embodiment. The gas sensor 104 includes a laminate 10 of positive temperature coefficient (PTC) thermistor ceramic, a catalytic electrode 112, an ohmic electrode 111, an internal electrode 32, and external electrodes 33 and 34.

Unlike the first to the third embodiments, a PTC thermistor ceramic is used in the fourth embodiment. The ceramic generally used as a PTC thermistor forms no ohmic contact with a Pd electrode which performs the catalytic reaction with a detection target gas, and hence, the ohmic electrode 111 which forms an ohmic contact with a PTC thermistor ceramic is provided between the catalytic electrode 112 and the thermistor layer. By the structure described above, heat generated by the catalytic electrode 112 is directly transferred to the thermistor layer through the ohmic electrode 111, and a higher response can be obtained.

A material for the ohmic electrode 111 and the internal electrode 32 is, for example, Ni, Cu, or an alloy thereof and forms ohmic contact with a PTC thermistor ceramic. In addition, as a material for the external electrodes 33 and 34, for example, Cr, Ni—Cu, or Ag may be used.

A particular example of a method for manufacturing this gas sensor 104 will be sequentially described. (a) As a ceramic raw material, a predetermined amount of BaO, $TiO_2$, $SrCO_3$, a rare earth oxide, such as $La_2O_3$, $Nd_2O_3$, or $Sm_2O_3$, an alkaline earth metal oxide, such as CaO, or a transition metal oxide, such as $Mn_3O_4$, is measured and is then charged into a ball mill containing pulverization media formed, for example, of zirconia. Next, after sufficient wet pulverization is performed, calcination is performed at a predetermined temperature, so that a ceramic powder is formed.

(b) After an organic binder is added to the ceramic powder, a wet mixing treatment is performed to form a slurry, and ceramic green sheets are then formed by a doctor blade method or the like.

(c) By using an internal-electrode paste containing Ni as a primary component or an internal-electrode paste containing Ni, Cu, or an alloy thereof, screen printing is performed on one ceramic green sheet to form an internal electrode pattern.

In a manner similar to that described above, an internal-electrode paste containing Ni as a primary component or an internal-electrode paste containing Ni, Cu, or an alloy thereof is screen-printed on one ceramic green sheet to form an ohmic electrode pattern. In addition, on this printed ohmic electrode pattern, a Pd-electrode paste is screen-printed to form a catalytic electrode pattern.

(d) The ceramic green sheet on which the internal electrode pattern is screen-printed is provided on the ceramic green sheet on which the ohmic electrode pattern and the catalytic electrode pattern are screen-printed, and a predetermined number of ceramic green sheets on which the internal electrode pattern and the catalytic electrode pattern are not printed are further laminated on the ceramic green sheet on which the internal electrode pattern is screen-printed and are then pressure bonded, so that a laminated substrate before sintering is formed.

Between the ceramic green sheet on which the internal electrode pattern and the ohmic electrode pattern are printed and the ceramic green sheet on which the catalytic electrode pattern is printed, a ceramic green sheet on which the internal electrode pattern and the catalytic electrode pattern are not printed may also be provided.

(e) After the laminated substrate which is a collective substrate before sintering is cut into the individual laminates 10, and a debinder treatment is performed on each laminate 10 received in a zirconia-made container, a firing treatment is performed at a predetermined temperature (for example, at 1,000° C. to 1,300° C.), so that the laminate 10 of PTC thermistor ceramics is formed.

(f) The external electrodes 33 and 34 are formed, for example, from Cr, Ni—Cu, or Ag, at two end portions of each laminate 10 by a thin film-forming method, such as a sputtering method or a vacuum deposition method. By the steps described above, the gas sensor 104 is manufactured.

In this embodiment, although an oxide, such as BaO, is used as the ceramic raw material, a carbonate or a hydroxide of Ba, for example, may also be used.

The remaining structure is the same as that of the gas sensor 101 shown in FIG. 3. In addition, the basic manufacturing method is similar to that described in the first embodiment.

According to the fourth embodiment, a layer of the catalytic electrode 112 functions as a catalytic electrode and has an ohmic contact with a PTC thermistor ceramic through a layer of the ohmic electrode 111. Hence, although a PTC thermistor is used, the catalytic electrode may be a single electrode to detect the resistance of the thermistor layer.

In addition, since a PTC thermistor is used as the thermistor layer, a high temperature coefficient of resistance is obtained, and with respect to the same change in temperature, a larger change in output signal is obtained. Accordingly, the sensitivity and the response are improved.

In addition, the resistance of the thermistor can be decreased, and output signal noise can be decreased.

The embodiments described above may be used in combination. For example, the structure may be formed in such a way that the temperature compensating internal electrodes 16 and 17 shown in FIG. 5 are formed in the gas sensor 101 or 102 shown in FIG. 2 or FIG. 4, respectively, the temperature compensating internal electrode 16 is electrically connected to the external electrode 13, and the other temperature compensating internal electrode 17 is extended to the bottom surface of the laminate 10 through a via. In addition, the hollow portion 15 shown in FIG. 4 may be formed in the gas sensor 104 shown in FIG. 6. Also, the structure may be formed in such a way that the temperature compensating internal electrodes 16 and 17 shown in FIG. 5 are formed in the gas sensor 104 shown in FIG. 5, the temperature compensating internal electrode 16 is electrically connected to the external electrode 33, and the other temperature compensating internal electrode 17 is extended to the bottom surface of the laminate 10 through a via.

FIFTH EMBODIMENT

Figure 7:
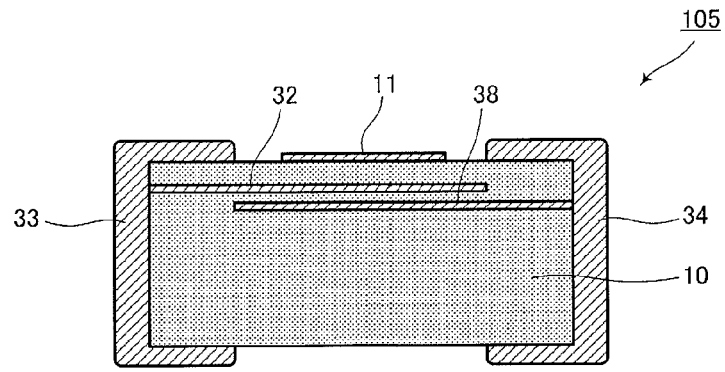
FIG. 7 is a cross-sectional view of a gas sensor 105 according to a fifth embodiment.

FIG. 7 is a cross-sectional view of a gas sensor 105 according to a fifth embodiment. The gas sensor 105 includes a laminate 10 of positive temperature coefficient (PTC) thermistor ceramic, a catalytic electrode 11, internal electrodes 32 and 38, and external electrodes 33 and 34.

In the laminate 10, a surface layer portion from the internal electrode 38 to an exposed portion of the catalytic electrode 11 is a sensing portion. When the catalytic electrode 11 comes into contact with a detection target gas, exothermic or endothermic heat is generated by a catalytic reaction. Accordingly, the temperature of a thermistor layer immediately under the catalytic electrode 11 is increased, and the resistance of a thermistor layer between the internal electrodes 32 and 38 is decreased.

The catalytic electrode 11 is not directly connected to the internal electrodes 32 and 38 in this embodiment. That is, the catalytic electrode 11 is not used to detect the resistance of the thermistor layer of the sensing portion. The internal electrodes 32 and 38 are electrically connected to the external electrodes 33 and 34, respectively. Hence, the resistance of the thermistor layer provided between the internal electrodes 32 and 38 is detected by the external electrodes 33 and 34.

The above thermistor ceramic is, for example, a PTC thermistor ceramic such as a BT-based semiconductor ceramic, the resistance of which changes in accordance with the change in temperature, and may also contain, for example, a rare earth element, such as strontium for CP adjustment, and/or manganese for improvement in properties.

Since the internal electrodes 32 and 38 are able to determine resistance based on the overlapping area and distance therebetween, the overlapping area and distance between the internal electrodes 32 and 38 are adjusted in accordance with the rate of change in resistance of the ceramic in order to obtain a desired resistance.

The catalytic electrode 11 is formed from a material which causes an exothermic or an endothermic reaction by interaction with a detection target gas, and for example, an oxidation catalytic material which catalyzes oxidation of a detection target gas and a hydrogen storing alloy may be used. By using the materials for the catalytic electrode described above, the gas to be detected may be appropriately selected. In particular, when the detection target gas is a hydrogen gas, Pt or Pd is preferably used in view of reactivity with a hydrogen gas.

Although this catalytic electrode 11 may be formed by sputtering or the like after sintering of the ceramic, a method, such as screen printing, is preferably performed on the ceramic green sheet before sintering from the view of process simplification and the like. In order to improve the catalytic efficiency, the catalytic electrode may be formed of a porous material. In this case, a binder component may be added to a screen printing paste, or other methods may also be used. In addition, in order to ensure the adhesion to the ceramic, the screen printing paste may contain an oxide component also contained in the ceramic. The steps of manufacturing this gas sensor 105 other than the step of forming a catalytic electrode are similar to those described in the fourth embodiment.

According to the fifth embodiment, the following particular advantages can be obtained. Since the catalytic electrode 11 generates exothermic or endothermic heat from a detection target gas and does not form an ohmic contact with the thermistor layer, even if a PTC thermistor is used as the thermistor ceramic, a noble metal itself, such as Pt or Pd, may be used for the catalytic electrode 11. That is, a layer of the ohmic electrode 111 of the fourth embodiment shown in FIG. 6 is not required. Hence, the process for forming a laminated structure can be simplified, and the cost can be reduced.

In addition, the exothermic heat or endothermic heat generated by the catalytic electrode 11 according to this structure is prevented from being directly transferred to the external electrodes 33 and 34 through the thermistor layer. Accordingly, a high response can be obtained.

Although the example is described in which a PTC thermistor ceramic is used, the present invention may also be applied to the case in which an NTC thermistor ceramic is used.

SIXTH EMBODIMENT

Figure 8:
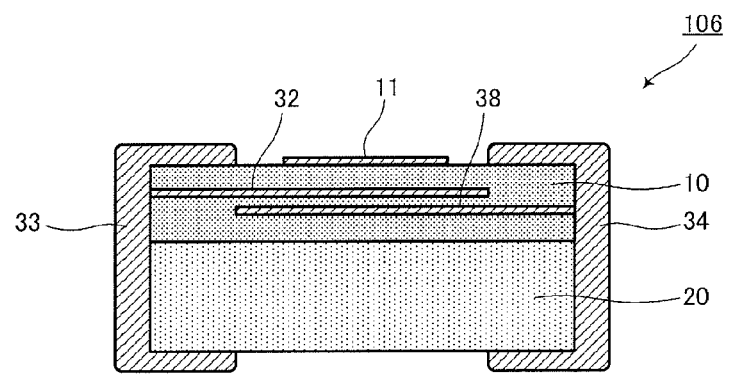
FIG. 8 is a cross-sectional view of a gas sensor 106 according to a sixth embodiment.

FIG. 8 is a cross-sectional view of a gas sensor 106 according to a sixth embodiment. The gas sensor 106 includes a laminate 10 of positive temperature coefficient (PTC) thermistor ceramic, a laminate 20 of insulating ceramic, a catalytic electrode 11, internal electrodes 32 and 38, and external electrodes 33 and 34.

Unlike the structure of the fifth embodiment shown in FIG. 7, a region of the laminate opposite to a region in which the catalytic electrode is formed with respect to an internal electrode located furthest away from the catalytic electrode among the plurality of internal electrodes is formed of the laminate 20 of insulating ceramics.

The ceramic layer opposite to the region in which the catalytic layer is formed with respect to the internal electrode 38 located furthest away from the catalytic electrode is located in a region which has no direct contribution to a sensing region of the gas sensor. When thermistor ceramic layers are present in this portion, the resistances thereof are equivalently connected in parallel between the external electrodes 33 and 34. Hence, as shown in FIG. 8, when a region having no direct contribution to the sensing region of the gas sensor is formed of insulating ceramic layers, the contribution of the change in resistance to gas detection in the sensing region can be increased, and higher sensitivity can be obtained.

A particular example of a method for manufacturing this gas sensor 106 will be sequentially described. (a) As a ceramic raw material, a predetermined amount of at least one of BaO, $TiO_2$, $SrCO_3$, a rare earth oxide, such as $La_2O_3$, $Nd_2O_3$, or $Sm_2O_3$, an alkaline earth metal oxide, such as CaO, and a transition metal oxide, such as $Mn_3O_4$, is measured and is then charged into a ball mill containing pulverization media formed, for example, of zirconia. Next, after sufficient wet pulverization is performed, calcination is performed at a predetermined temperature, so that a ceramic powder is formed.

(b) After an organic binder is added to the ceramic powder, a wet mixing treatment is performed to form a slurry, and ceramic green sheets are then formed by a doctor blade method or the like.

(c) By using an internal-electrode paste containing Ni as a primary component or an internal-electrode paste containing Ni, Cu, or an alloy thereof, screen printing is performed on one ceramic green sheet to form an internal electrode pattern. In addition, on one ceramic green sheet, a Pd-electrode paste is screen-printed to form a pattern of the catalytic electrode 11.

(d) The ceramic green sheet on which the internal electrode pattern is screen-printed is provided on the ceramic green sheet on which the pattern of the catalytic electrode 11 is screen-printed, and a predetermined number of ceramic green sheets on which the internal electrode pattern and the catalytic electrode pattern are not printed are further laminated on the ceramic green sheet on which the internal electrode pattern is screen-printed and are then pressure bonded, so that a laminate is formed.

(e) A predetermined number of green sheets formed, for example, of a BT-based ($BaTiO_3$-based) ceramic containing Ca or the like and having insulating properties after firing are laminated on the laminate and are then pressure bonded, so that a collective substrate before sintering is formed.

(f) After the collective substrate before sintering is cut into individual laminates, and a debinder treatment is performed on each laminate received in a zirconia-made container, a firing treatment is performed at a predetermined temperature (for example, at 1,000° C. to 1,300° C.), so that a collective including the laminate 10 of PTC thermistor ceramic and the laminate 20 of insulating ceramic is formed.

(g) The external electrodes 33 and 34 are formed, for example, from Cr, Ni—Cu, or Ag, at two end portions of the collective by a thin film-forming method, such as a sputtering method or a vacuum deposition method. By the steps described above, the gas sensor 106 is manufactured.

Although the example is described in this embodiment is one in which a PTC thermistor ceramic is used, the present invention may also be applied to the case in which an NTC thermistor ceramic is used.

SEVENTH EMBODIMENT

Figure 9:
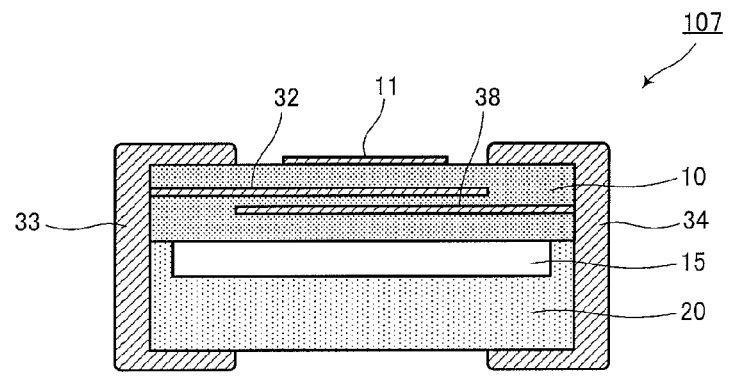
FIG. 9 is a cross-sectional view of a gas sensor 107 according to a seventh embodiment.

FIG. 9 is a cross-sectional view of a gas sensor 107 according to a seventh embodiment. The gas sensor 107 includes a laminate 10 of positive temperature coefficient (PTC) thermistor ceramic, a laminate 20 of insulating ceramic, a hollow portion 15, a catalytic electrode 11, internal electrodes 32 and 38, and external electrodes 33 and 34. The structure other than the hollow portion 15 is similar to that of the sixth embodiment shown in FIG. 8.

The hollow portion 15 thermally separates a sensing portion, which includes a surface layer portion of the laminate 10 in which the catalytic electrode and the internal electrode are located, from the other region of an element main body. This hollow portion 15 is formed in such a way that some of insulating layers forming the laminate 20 are processed to have an opening portion and are then laminated to each other.

When the catalytic electrode 11 comes into contact with a detection target gas and generates heat thereby, the heat is also transferred to thermistor layers located opposite to the catalytic electrode with respect to the internal electrode 32; however, since the hollow portion 15 is provided in a region located further apart from the catalytic electrode, heat conduction is blocked at this place, and hence the heat is prevented from spreading over the entire laminates 10 and 20. In other words, the heat capacity of the sensing portion is small. As a result, the rate of increase in temperature of the sensing portion by a catalytic reaction of a detection target gas is increased, and a high response can be obtained.

A method for manufacturing this gas sensor 107 is similar to that of the sixth embodiment other than the formation of the hollow portion 15. The ceramic green sheets forming the hollow portion are formed in such a way that holes forming the hollow portion are provided in the ceramic green sheets, for example, by a laser or a punching process and are then filled, for example, with an organic material, such as a binder, or a carbon paste. As a result, the ceramic green sheets each having a hollow pattern are formed.

In addition, a predetermined number of layers of insulating ceramic green sheets are formed into the ceramic green sheets each having a hollow pattern.

Although this example is described in which a PTC thermistor ceramic is used, the present invention may also be applied to the case in which an NTC thermistor ceramic is used.

EIGHTH EMBODIMENT

Figure 10:
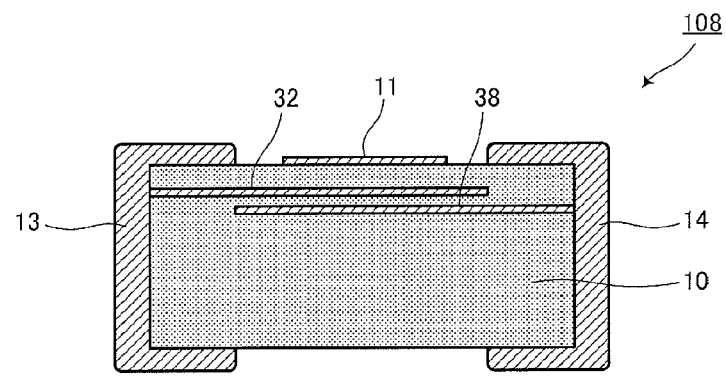
FIG. 10 is a cross-sectional view of a gas sensor 108 according to an eighth embodiment.

FIG. 10 is a cross-sectional view of a gas sensor 108 according to an eighth embodiment. The gas sensor 108 includes a laminate 10 of positive temperature coefficient (PTC) thermistor ceramic, a catalytic electrode 11, internal electrodes 32 and 38, and external electrodes 13 and 14.

In the laminate 10, a surface layer portion from the internal electrode 38 to an exposed portion of the catalytic electrode 11 is a sensing portion. When the catalytic electrode 11 comes into contact with a detection target gas, exothermic heat or endothermic heat is generated by a catalytic reaction. Accordingly, the temperature of a thermistor layer immediately under the catalytic electrode 11 is increased, and the resistance of the thermistor layer between the internal electrodes 32 and 38 is decreased.

A material for the internal electrodes 32 and 38 is, for example, a base metal, such as Ni, Cu, or an alloy thereof. Hence, the internal electrodes 32 and 38 each form an ohmic contact with a PTC thermistor ceramic. On the other hand, a material for the external electrodes 13 and 14 is a noble metal, such as Ag, Pd, or an alloy thereof, and forms no ohmic contact with a PTC thermistor ceramic. Accordingly, although the external electrodes 13 and 14 are electrically connected to the internal electrodes 32 and 38, respectively, the interface with the PTC thermistor ceramic has a higher interface resistance than the resistance of the sensing portion. Since the resistance of the PTC thermistor ceramic layer between the internal electrodes 32 and 38 becomes dominant, and the contribution of the change in resistance to gas detection in the sensing region can be increased, higher sensitivity can be obtained.

In the case in which an NTC thermistor ceramic is used as the thermistor ceramic, when a base metal, such as Cu, Ni, or an alloy thereof, is used as the external electrode, advantages similar to those described above may also be obtained even by using an NTC thermistor ceramic.

NINTH EMBODIMENT

Figure 11:
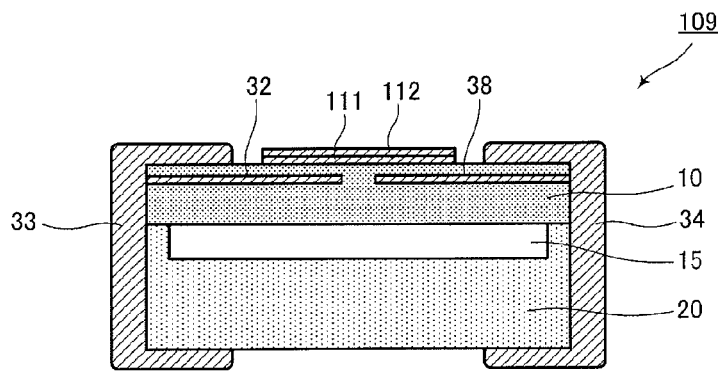
FIG. 11 is a cross-sectional view of a gas sensor 109 according to a ninth embodiment.

FIG. 11 is a cross-sectional view of a gas sensor 109 according to a ninth embodiment. The gas sensor 109 includes a laminate 10 of positive temperature coefficient (PTC) thermistor ceramic, a laminate 20 of insulating ceramic, a hollow portion 15, an ohmic electrode layer 111, a catalytic electrode 112, internal electrodes 32 and 38, and external electrodes 33 and 34.

The ohmic electrode layer 111 in ohmic contact with a PTC thermistor ceramic is provided as in the case of the gas sensor 104 shown in FIG. 6. In addition, the laminate 20 of insulating ceramic and the hollow portion 15 are provided as in the case of the gas sensor 107 shown in FIG. 9.

When the catalytic electrode 112 in FIG. 11 comes into contact with a detection target gas and generates heat thereby, the temperature of the thermistor ceramic layer between the ohmic electrode layer 111 and the internal electrodes 32 and 38 is increased, and in accordance with this increase, the resistance between the internal electrodes 32 and 38 through the ohmic electrode layer 111 is changed.

That is, the internal electrodes 32 and 38 are present in the same layer, and the thermistor ceramic layer located between the internal electrodes 32 and 38 and the ohmic electrode layer 111 is a sensing portion. Since the sensing portion can be made thin (shallow) according to this structure, the heat capacity of the sensing portion can be further decreased, and hence a higher response can be obtained.

Although the example described is one in which a PTC thermistor ceramic is used, the present invention may also be applied to the case in which an NTC thermistor ceramic is used.

10—laminate of thermistor ceramics
11—catalytic electrode
12—internal electrode
13, 14—external electrode
15—hollow portion
16, 17—temperature compensating internal electrode
20—laminate of insulating ceramic
21—surface electrode
22, 23—rear electrode
24, 25, 26—via electrode
32, 38—internal electrode
33, 34—external electrode
101 to 109—gas sensor
111—ohmic electrode layer
112—catalytic electrode layer

The invention claimed is:

1. A gas sensor comprising a laminate which includes a plurality of electrodes and a plurality of thermistor layers,
    wherein one of the plurality of electrodes constitutes a catalytic electrode which is disposed at a surface of the laminate and catalyzes an exothermic or an endothermic reaction when coming into contact with a detection target gas, and
    a different one of the plurality of electrodes is an internal electrode which is disposed so that at least one of the plurality of thermistor layers is between the internal electrode and the catalytic electrode
    further comprising a hollow portion disposed in a portion of the laminate on the side of the internal electrode remote from the catalytic electrode,
    wherein at least two of the plurality of electrodes are temperature compensating internal electrodes which are disposed so that at least one of the plurality of thermistor layers is disposed therebetween and not thermally coupled with the catalytic electrode.

2. The gas sensor according to claim 1, having an insulation region disposed on a side of the internal electrode located furthest apart from the catalytic electrode which is opposite a side thereof facing the catalytic electrode.

3. The gas sensor according to claim 2,
    further comprising an external electrode disposed at a side surface of the laminate so as to be electrically connected to the internal electrode, wherein the external electrode does not form ohmic contact with the plurality of thermistor layers.

4. The gas sensor according to claim 3,
    having an ohmic electrode between the catalytic electrode and the laminate surface on which the catalytic electrode is disposed, said ohmic electrode being in ohmic contact with said laminate surface.

5. The gas sensor according to claim 2,
    having an ohmic electrode between the catalytic electrode and the laminate surface on which the catalytic electrode is disposed, said ohmic electrode being in ohmic contact with said laminate surface.

6. The gas sensor according to claim 1,
having an ohmic electrode between the catalytic electrode and the laminate surface on which the catalytic electrode is disposed, said ohmic electrode being in ohmic contact with said laminate surface.

7. The gas sensor according to claim 1, further comprising an external electrode disposed at a side surface of the laminate so as to be electrically connected to the internal electrode, wherein the external electrode does not form ohmic contact with the plurality of thermistor layers.

8. A gas sensor comprising a laminate which includes a plurality of electrodes and a plurality of thermistor layers,
wherein one of the plurality of electrodes constitutes a catalytic electrode which is disposed at a surface of the laminate and catalyzes an exothermic or an endothermic reaction when coming into contact with a detection target gas,
a different one of the plurality of electrodes is an internal electrode which is disposed so that at least one of the plurality of thermistor layers is between the internal electrode and the catalytic electrode,
wherein there is no insulating layer between the catalytic electrode and a thermistor layer adjacent thereto, and
wherein at least two of the plurality of electrodes are temperature compensating internal electrodes disposed so that at least one of the plurality of thermistor layers is disposed therebetween and is not thermally coupled with the catalytic electrode.

9. The gas sensor according to claim 8, having an ohmic electrode between the catalytic electrode and the laminate surface on which the catalytic electrode is disposed, said ohmic electrode being in ohmic contact with said laminate surface.

10. The gas sensor according to claim 8, further comprising an external electrode disposed at a side surface of the laminate so as to be electrically connected to the internal electrode, wherein the external electrode does not form ohmic contact with the plurality of thermistor layers.

11. The gas sensor according to claim 8, wherein the thermistor layers are negative temperature coefficient thermistor layers.

12. The gas sensor according to claim 8, wherein the thermistor layers are positive temperature coefficient thermistor layers.

13. The gas sensor according to claim 8, wherein the catalytic electrode comprises a catalyst for an exothermic or endothermic reaction with hydrogen.

14. The gas sensor according to claim 13, wherein the catalytic electrode comprises a catalyst for an exothermic or endothermic reaction with hydrogen comprises Pd or Pt.

15. The gas sensor according to claim 8, further comprising a hollow portion disposed in a portion of the laminate on the side of the internal electrode remote from the catalytic electrode.

16. The gas sensor according to claim 15,
having an ohmic electrode between the catalytic electrode and the laminate surface on which the catalytic electrode is disposed, said ohmic electrode being in ohmic contact with said laminate surface.

17. The gas sensor according to claim 15, further comprising an external electrode disposed at a side surface of the laminate so as to be electrically connected to the internal electrode, wherein the external electrode does not form ohmic contact with the plurality of thermistor layers.

18. The gas sensor according to claim 15, having an insulation region disposed on a side of the internal electrode located furthest apart from the catalytic electrode opposite a side thereof facing the catalytic electrode.

* * * * *